United States Patent [19]

Scharbert

[11] Patent Number: 5,259,933
[45] Date of Patent: Nov. 9, 1993

[54] PROCESS FOR OXIDIZING HYDROXYMETHYLPYRIDINE DERIVATIVES TO PYRIDINECARBOXYLIC ACID DERIVATIVES AT NICKEL OXIDE HYDROXIDE ANODES

[75] Inventor: Bernd Scharbert, Frankfurt am Main, Fed. Rep. of Germany

[73] Assignee: Hoechst Aktiengesellschaft, Frankfurt am Main, Fed. Rep. of Germany

[21] Appl. No.: 946,190

[22] Filed: Sep. 17, 1992

[30] Foreign Application Priority Data

Sep. 19, 1991 [DE] Fed. Rep. of Germany ....... 4131220

[51] Int. Cl.⁵ .................................. C25B 3/02
[52] U.S. Cl. .................................. 204/78; 204/290 R; 204/291; 204/292; 204/293; 204/294; 205/333
[58] Field of Search .................... 204/78, 290 R, 291, 204/292, 293, 294; 205/333

[56] References Cited

U.S. PATENT DOCUMENTS

| | | | |
|---|---|---|---|
| 3,291,805 | 12/1966 | Ondetti et al. | 546/294 |
| 4,411,746 | 10/1983 | Degner et al. | 204/78 |
| 4,482,439 | 11/1984 | Toomey, Jr. | 204/78 |
| 4,693,793 | 9/1987 | Alfenaar et al. | 204/75 |

OTHER PUBLICATIONS

Baizer, *Organic Electrochemistry*, 1973, pp. 599–600.
D. C. Trivedi et al., "Transition Metal Oxide Anodes and Their Application in the Synthesis of Organic Compounds," Chemical Abstracts, 98:169227p (1983).

*Primary Examiner*—C. Warren Ivy
*Assistant Examiner*—Zinna N. Davis
*Attorney, Agent, or Firm*—Finnegan, Henderson, Farabow, Garrett & Dunner

[57] ABSTRACT

Process for oxidizing hydroxymethylpyridine derivatives to pyridinecarboxylic acid derivatives at nickel oxide hydroxide anodes A process is described for oxidizing o-hydroxymethylpyridine derivatives into their pyridinecarboxylic acid derivatives at nickel oxide hydroxide anodes.

12 Claims, No Drawings

PROCESS FOR OXIDIZING HYDROXYMETHYLPYRIDINE DERIVATIVES TO PYRIDINECARBOXYLIC ACID DERIVATIVES AT NICKEL OXIDE HYDROXIDE ANODES

The invention relates to a process for oxidizing o-hydroxymethylpyridine derivatives to pyridinecarboxylic acid derivatives.

It is known that hydroxymethylpyridines can be oxidized to the corresponding carboxylic acids using $KMnO_4$ (DD-A-248 119). In many other processes, the reaction of hydroxymethylpyridines with permanganate is the chosen method of oxidation [Pharmazie 39 (1984), 155, BE-A-866 977, JP-A-063 434, U.S. Pat. No. 3,291,805]. For industrial application, this method has, however, serious disadvantages. Thus, $KMnO_4$ is an expensive oxidizing agent and the manganese dioxide produced has to be disposed of after the reaction.

In another process, nitric acid in concentrated sulfuric acid is used as oxidizing agent. A disadvantage of these processes is that the reaction conditions have to be extreme (15 h at 160°–180° C.) and the entire reaction solution has to be brought to a pH of 2 for working-up, in which process a very high salt load is produced.

There are also processes in which the carboxylic acid is prepared via the corresponding aldehyde in a two-stage oxidation. In this case, however, expensive and toxic reagents such as selenium dioxide or lead tetraacetate are used. These methods have therefore not been extrapolated to an industrial scale.

In Example 14, U.S. Pat. No. 4,482,439 teaches the electrochemical oxidation of 4-hydroxymethylpyridine at $PbO_2$ anodes in a cell partitioned by an ion exchanger membrane. With this process, however, it is not possible to oxidize the hydroxymethyl function selectively without concomitantly oxidizing other substituents on the pyridine ring at the same time.

It was therefore the object of the present invention to provide a process for selectively oxidizing o-hydroxylmethylpyridine derivatives to the corresponding pyridinecarboxylic acid derivatives, which process is technically simple to carry out and produces the required product in good yields. The selectivity of the process should manifest itself in the fact that other substituents on the pyridine ring, such as alkyl or alkoxy groups are not oxidized simultaneously.

The object is achieved by a process in which a hydroxymethylpyridine derivative of the formula I

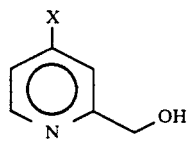

where

X is hydrogen, $(C_1-C_{12})$alkyl, $(C_6-C_{12})$aryl, $COOR^1$, $CONH_2$, $CONHR^1$, $CON(R^1)_2$, CN, $C(O)R^1$, $SO_2R^1$, $SO_3H$ or $NO_2$, where $R^1$ is hydrogen, $(C_1-C_{12})$alkyl, $(C_6-C_{12})$aryl, is converted into a compound of the formula II

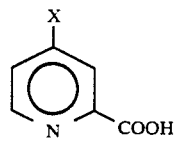

which process comprises oxidizing the compound represented by formula I electrochemically at NiO(OH) anodes.

The process according to the invention is preferred for oxidizing compounds of the formula I in which X is hydrogen, $(C_1-C_{12})$alkyl, $(C_6-C_{12})$aryl, $COOR^1$, $CONH_2$, $CONHR^1$, $CON(R^1)_2$ and $C(O)R^1$.

In particular, those compounds of the formula I are oxidized in which X is hydrogen, $(C_1-C_6)$alkyl, phenyl or naphthyl, $COOR^1$, $CONH_2$, $CONHR^1$, $CON(R^1)_2$ and $C(O)R^1$.

$R^1$ is preferably $(C_1-C_6)$alkyl, phenyl or naphthyl.

The material of the anode electrode is composed of carbon or metal and is coated in all cases with a layer of NiO(OH). Of the metal electrodes, steel or nickel electrodes coated with NiO(OH) are preferred.

In this connection, the formation of the NiO(OH) layer is carried out by cathodically depositing nickel on the electrode materials mentioned from an aqueous solution of soluble nickel salts having a concentration of nickel ions of between 0.01 and 2 mol/l, preferably between 0.05 and 1 mol/l, then exchanging the nickel salt solution for an aqueous alkaline solution having a concentration of alkali-metal hydroxide of between 0.001 and 2 mol/l, preferably between 0.01 and 1 mol/l, and anodically polarizing the electrode materials mentioned with the nickel deposited.

Both the cathodic nickel deposition and the anodic polarization prior to the electrode oxidation of the compound represented by formula I are carried out for 5 to 120 minutes, preferably 20 to 40 minutes, at a current density of between 1 and 100 $mA/cm^2$, preferably between 2 and 10 $mA/cm^2$.

The material of the cathode electrode should ensure that hydrogen is liberated under the specified electrolysis conditions. Preferred for this purpose are nickel, palladium, platinum or steel.

In principle, the process according to the invention can be carried out in a partitioned or unpartitioned elec-trode cell. If a partitioned cell is used, all types of ion exchanger membranes or, alternatively, inorganic materials are suitable for the purpose of partitioning.

As electrolyte (in the unpartitioned cell) or anolyte (in the partitioned cell), use is made of aqueous solutions which contain 0.001 to 2 mol/l, preferably between 0.01 and 1 mol/l, alkali-metal hydroxide, preferably NaOH. The concentration of the compound represented by formula I is between 0.001 and 10 mol/l, preferably between 0.01 and 0.5 mol/l.

The electrolysis temperature is between 5° and 100° C., preferably between 15° and 70° C., and the current density is between 1 and 50 mA/cm,, preferably between 2 and 20 $mA/cm^2$.

The electrolysis can be carried out until conversion is complete. The conversion can be monitored by means of HPLC analysis. It is possible, but not preferred, to discontinue the electrolysis when conversion is incomplete and then to isolate the starting material and the product.

The working-up is carried out by neutralizing until the isoelectric point of the corresponding carboxylic acid is reached. In this process, the carboxylic acid precipitates. Yields which are somewhat higher still are obtained if the electrolysis product is filtered through a strongly acidic ion exchanger resin. The aqueous filtrate contains the pure compound represented by formula II. In order to extract further compounds represented by formula II adsorbed on the resin, the resin is then washed with methanol. The methanol filtrate and the aqueous filtrate are each evaporated to dryness and, when combined, result in a high yield of the compound represented by formula II.

If the compound represented by formula I contains an ester function ($X=COOR^1$) it is unstable under the electrolysis conditions and has to be hydrolyzed prior to the electrolysis, with the alcohol $R^1OH$ released being removed. Hydrolysis during the electrolysis would result in the alcohol $R^1OH$ released being oxidized at the NiO(OH) anode in the same way as the compound represented by formula I. The oxidation of the alcohol $R^1OH$ would compete with the oxidation of the compound represented by formula I. A lowering of the current efficiency would be the result.

The procedure during hydrolysis is to bring the aqueous alkaline solution made up for the electrolysis to a temperature of between 50° and 100° C., preferably between 70° and 90° C., for 1 to 60 minutes, preferably 5 to 10 minutes.

The aqueous alkaline solution is extracted with an organic solvent, preferably dichloromethane or ethyl acetate and the aqueous phase is stored. In the case of alcohols $R^1OH$ having a boiling point of less than 100° C., between 1 and 10% by volume, preferably between 3 and 5% by volume, of the solution may also be evaporated. In this case, the alcohol component is contained in the component removed. In the case of alcohols $R^1OH$ having a boiling point of less than 100° C., the last mentioned method is preferred.

In this procedure, regardless of the versions mentioned above, the remaining solution contains the compound represented by formula I in which $X=COOH$ or, in alkaline medium, $COO^-M^+$ ($M$=alkali metal), and no longer any free alcohol $R^1OH$. It can be used for the electrolysis.

The process according to the invention is remarkable for the fact that compounds represented by formula I are converted virtually quantitatively. The preparation of the starting materials represented by the formula I is described in U.S. patent application Ser. No. 07/945,943, filed Sep. 17, 1992, which is filed simultaneously. The reaction conditions and the working-up are easy to carry out industrially.

In the oxidation according to the invention, the substituents X on the pyridine ring are not attacked. In particular, the electrochemical process of the prior art using $PbO_2$ anodes cannot be applied in the case of compounds containing the oxidizable substituents $X=C(O)R^1$ and $R^1$ since these substituents are oxidatively transformed. Furthermore, it was found that the compound represented by formula I in which $X=COOR^1$ can only be produced in yields of less than 70% by the prior art process described (Comparison Example A). Surprisingly, yields of more than 96% (HPLC analysis) and isolated yields of more than 90% are achieved by the process according to the invention.

It should furthermore be emphasized that the compound represented by formula I in which $X=COOR^1$ is slowly hydrolyzed during electrolysis by the prior art process and, consequently, a mixture of products represented by formula II in which $X=COOH$ and $COOR^1$ is produced.

For example, pyridine-2,4-dicarboxylic acid can be prepared by the process according to the invention from the compound represented by formula I in which $X=COOR^1$. According to DE-A-3,432,094, compounds of this type are intermediates for compounds which are used to inhibit proline and lysine hydroxylase.

The invention will be explained in greater detail by reference to the examples cited below.

Formation of the anode

Electrolysis is carried out for 30 minutes in an unpartitioned cell at a current density of 10 mA/cm² in a 0.2M $Ni(NO_3)_2$ solution with cathodic polarization of the nickel electrode in a cell having two oppositely situated, planar and equally large electrodes, one electrode being of nickel and the other of stainless steel, the back of each electrode being coated with glass. The electrolyte is then exchanged for a 0.1N NaOH solution and electrolysis is carried out for 30 minutes with anodic polarization of the nickel electrode as described above. A uniformly black coating indicates the formation of NiO(OH). Until the electrode is used, a low protective current in the region of 1 mA/cm² is maintained. Prior to being used for an electrochemical oxidation, the electrode is briefly rinsed with water.

EXAMPLE 1

1.67 g (0.01 mol) of 2-hydroxymethyl-4-carboxymethylpyridine are dissolved in 300 ml of 1N sodium hydroxide solution. 10 ml of the solution are evaporated at 90° C. and the remaining solution is poured into an unpartitioned glass-container cell containing an NiO(OH) anode and a stainless-steel cathode. Electrolysis is carried out at a temperature of 25° C. and a current density of 10 mA/cm². The yield of pyridine-2,4-dicarboxylic acid is determined by means of HPLC.

On passing 4 F/mol, the yield is 50%.
On passing 6 F/mol, the yield is 63%.
On passing 8 F/mol, the yield is 73%.

EXAMPLE 2

This example is as Example 1, but the current density during the electrolysis is 2.5 mA/cm².

On passing 2.7 F/mol, the yield is 38%.
On passing 8.5 F/mol, the yield is 84%.
On passing 11.8 F/mol, the yield is 96%.

EXAMPLE 3

This example is as Example 1, with the exception that the electrolysis is carried out until 8 F/mol have been passed at a current density of 10 mA/cm², then electrolysis is continued at a current density of 2.5 mA/cm² until 12 F/mol have been passed. The electrolysis product is filtered through a strongly acidic ion exchanger. After freeze drying, the eluate yields 0.83 g of pyridine-2,4-dicarboxylic acid. The ion exchanger resin is washed with methanol and the eluate is evaporated. 0.70 g of pyridine-2,4-dicarboxylic acid are left in the residue. The total yield is 9.2 mmol, equivalent to 92%.

EXAMPLE 4

This example is as Example 3, except that working-up is carried out in a different way. After electrolysis, the electrolysis product is brought to a pH of 1.5 with 5N HCl. The deposit precipitated is filtered off and dried. 1.48 g (8.9 mmol) of pyridine-2,4-dicarboxylic acid, equivalent to 89%, are left.

COMPARISON EXAMPLE A 1.67 g (0.01 mol) of 2-hydroxymethyl-4-carboxymethylpyridine in 100 ml of a 14%-strength sulfuric acid solution are electrolyzed at a current level of 1.0 A and at a temperature of 25° C. until a current consumption of 2.14 Ah (8 F/mol) is reached in an electrochemical cell partitioned by a cation exchanger membrane (®Nafion 324) and containing a PbO$_2$ heaped-bed anode (diameter 8 cm, height 1 cm) and a platinum cathode. The catholyte is composed of 7%-strength sulfuric acid. Pyridine-2,4-dicarboxylic acid is detected in a yield of 63% with the aid of HPLC analysis and 2-carboxy-4-methoxycarbonylpyridine is present in 6% yield. The starting compound is only present in traces of less than 2%.

I claim:

1. Process for selectively oxidizing hydroxymethylpyridine derivatives, in which a hydroxymethylpyridine derivative of the formula I

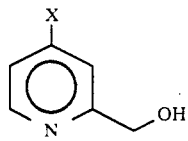

where
X is hydrogen, (C$_1$-C$_{12}$)alkyl, (C$_6$-C$_{12}$)aryl, COOR$^1$, CONH$_2$, CONHR$^1$, CON(R$^1$)$_2$, CN, C(O)R$^1$, SO$_2$R$^1$, SO$_3$H or NO$_2$, where
R$^1$ is hydrogen, (C$_1$-C$_{12}$)alkyl, (C$_6$-C$_{12}$)aryl,
is converted into a compound of the formula II

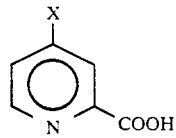

which process comprises oxidizing the compound represented by formula I electrochemically at NiO(OH) anodes, wherein, as electrolyte or anolyte, an aqueous solution containing 0.001 to 2 mol/l of alkali-metal hydroxide is used.

2. The process as claimed in claim 1, wherein a compound of the formula I in which
X is hydrogen, (C$_1$-C$_{12}$)alkyl, (C$_6$-C$_{12}$)aryl, COOR$^1$, CONH$_2$, CONHR$^1$, CON(R$^1$)$_2$ or C(O)R$^1$. is oxidised.

3. The process as claimed in claim 1, wherein a compound of the formula I in which
X is hydrogen, (C$_1$-C$_6$)alkyl, phenyl or naphthyl, COOR$^1$, CONH$_2$, CONHR$^1$, CON(R$^1$), and C(O)R$^1$ is oxidized.

4. The process as claimed in claim 1, wherein the oxidation is carried out at an anode which is composed of carbon or a metal, coated in all cases with a layer of NiO(OH).

5. The process as claimed in claim 1, wherein, for the formation of the NiO(OH) layer prior to the electrolysis, nickel is cathodically deposited on the electrode material from an aqueous solution of soluble nickel salts.

6. The process as claimed in claim 5, wherein the nickel salt solution is subsequently exchanged for an aqueous alkaline solution and the electrode material is anodically polarized.

7. The process as claimed in claim 6, wherein the cathode is composed of nickel, palladium, platinum or steel.

8. The process as claimed in claim 1, wherein the oxidation is carried out in a partitioned or unpartitioned electrolysis cell.

9. The process as claimed in claim 1, wherein the cathodic nickel deposition and the anodic polarization are carried out for 5 to 120 min, preferably 20 to 40 min, at a current density of between 1 and 100 mA/cm$^2$, preferably between 2 and 10 mA/cm$^2$.

10. The process as claimed in claim 1, wherein the oxidation is carried out at an electrolysis temperature of between 5° and 100° C. and at a current density of between 1 and 50 mA/cm$^2$.

11. The process as claimed in claim 1, wherein the aqueous solution contains 0.01 to 1 mol/l of alkali-metal hydroxide.

12. The process as claimed in claim 1, wherein the alkali-metal hydroxide is NaOH.

* * * * *

UNITED STATES PATENT AND TRADEMARK OFFICE
CERTIFICATE OF CORRECTION

PATENT NO. : 5,259,933
DATED : NOVEMBER 9, 1993
INVENTOR(S) : SCHARBERT

It is certified that error appears in the above-identified patent and that said Letters Patent is hereby corrected as shown below:

In Claim 3, at column 6, line 12, "$CON(R^1)$" should read --$CON(R^1)_2$--.

Signed and Sealed this

Sixth Day of September, 1994

Attest:

BRUCE LEHMAN

Attesting Officer     Commissioner of Patents and Trademarks